United States Patent [19]
Talen et al.

[11] Patent Number: 5,893,870
[45] Date of Patent: Apr. 13, 1999

[54] DEVICE AND METHOD FOR RESTRICTING VENOUS FLOW FOR IMPROVED BLOOD SAMPLING

[75] Inventors: David J. Talen, Plymouth; Scott P. Thome, Waite Park, both of Minn.

[73] Assignee: ActiLife L.L.C., Plymouth, Minn., MN

[21] Appl. No.: 08/897,488

[22] Filed: Jul. 21, 1997

[51] Int. Cl.⁶ .................................................. A61M 17/00
[52] U.S. Cl. .................................................. 606/201
[58] Field of Search ................................. 606/201–203; 600/573, 583

[56] References Cited

U.S. PATENT DOCUMENTS

| | | | |
|---|---|---|---|
| 1,592,479 | 7/1926 | Williams | 606/203 |
| 2,103,174 | 12/1937 | Posada | |
| 2,893,394 | 7/1959 | Thomsen | |
| 3,421,761 | 1/1969 | Grant | |
| 3,461,863 | 8/1969 | Sullinger | |
| 3,794,019 | 2/1974 | Ritland et al. | |
| 4,149,540 | 4/1979 | Hasslinger | |
| 4,899,737 | 2/1990 | Lazarian | |
| 4,911,162 | 3/1990 | Wolff | |
| 5,451,234 | 9/1995 | Wassermann | |
| 5,540,714 | 7/1996 | Payne, Jr. et al. | |

FOREIGN PATENT DOCUMENTS

| 122185 | 3/1927 | Switzerland | 606/203 |
|---|---|---|---|

*Primary Examiner*—William Lewis
*Attorney, Agent, or Firm*—Patterson & Keough, P.A.

[57] ABSTRACT

An apparatus used in a method of restricting venous flow in an extremity includes a first flexible, stretchable elongate band and a first flexible, stretchable loop fixed to a first end of the first band. A second loop sized to fit about the extremity is defined by passing a free end of the first band through the first loop. Upon pulling a free end of the first band through the first loop in a direction outward from the extremity, the first band stretches against the first loop, thereby causing the second loop to tighten about the extremity to restrict venous flow therethrough. A combination of frictional engagement and stretching of the first band and of the first loop against each other releasably secures the second loop about the extremity in its tightened position, thereby eliminating the need to hold the apparatus to maintain the tightened position. With venous flow restricted in the extremity, various procedures can be performed such as obtaining a blood sample with a conventional fingerstick puncture of the extremity.

8 Claims, 2 Drawing Sheets

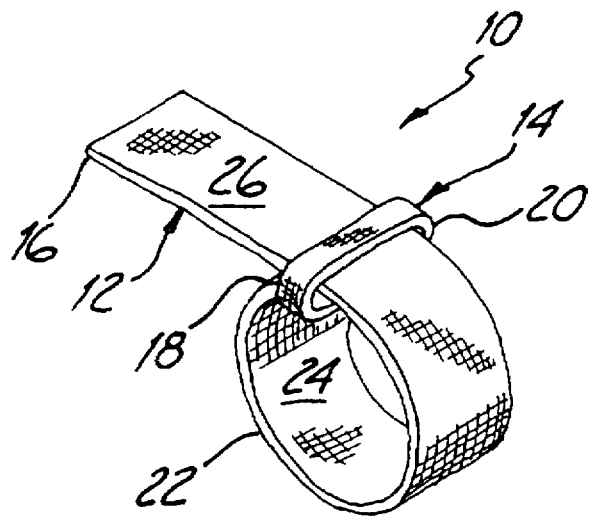
Fig. 1
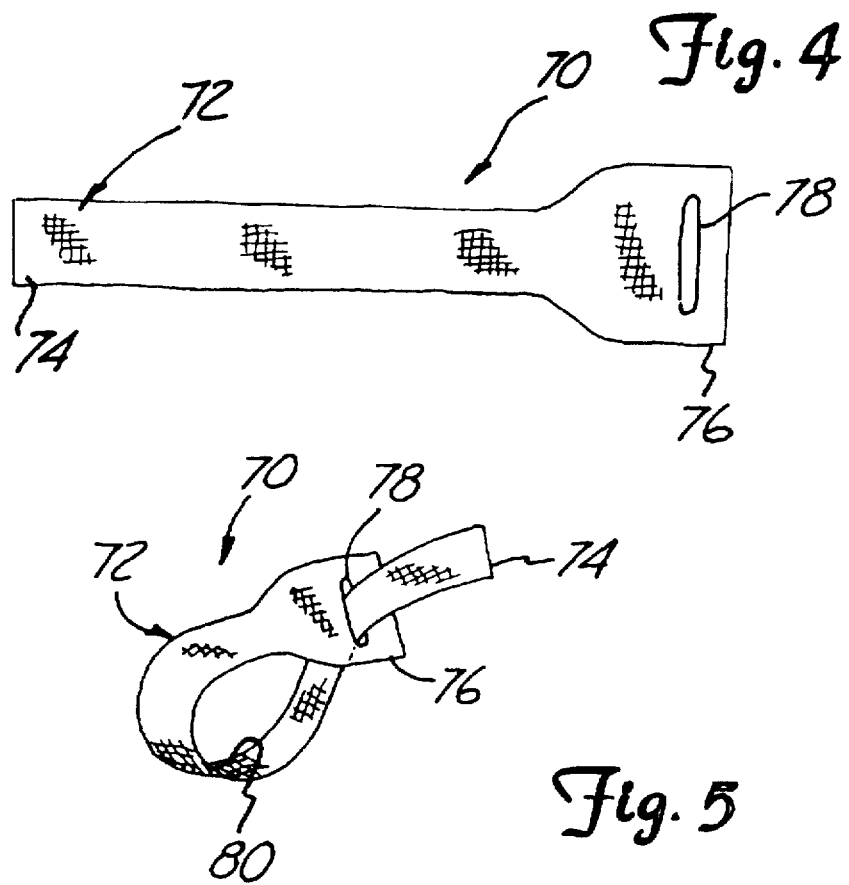
Fig. 4
Fig. 5

DEVICE AND METHOD FOR RESTRICTING VENOUS FLOW FOR IMPROVED BLOOD SAMPLING

BACKGROUND OF THE INVENTION

The present invention relates to the field of blood sampling, specifically in the area of blood glucose monitoring to help ensure adequate levels of capillary blood are collected for a glucose test.

Diabetes is a disease, which affects a large segment of the population. According to the American Diabetes Association (ADA), it is estimated that nearly 16 million people in the Unites States have diabetes. Today, however, approximately half of this figure or 8 million people have been diagnosed with the disease.

People with diabetes, in order to maintain their blood glucose in a "normal" range, must balance their level of exercise, their diet and their medication (insulin). In order to monitor an individual's effectiveness in maintaining these variables, an individual must measure their blood glucose up to 4 or more times per day. The tool that provides these individuals with a snapshot of their glucose level, and hence, a measurement of how well these variables are being balanced or managed, is the blood glucose monitor.

Self-monitoring of blood glucose (SMBG) was made possible during the late 1970's through the introduction of slow, technique dependent glucose meters. These glucose meters have since undergone significant improvement. Today, blood glucose meters are capable of providing a blood glucose reading in less than 30 seconds, are the size of a fountain pen and are relatively simple to use.

The technological advances in blood glucose meters and the increased awareness of the importance of maintaining glycemic control in avoiding the complications associated with diabetes have led to a dramatic increase in the number of individuals using blood glucose meters. Today, approximately 4 million individuals use blood glucose meters in the United States which equates to approximately 1.3 billion tests annually.

Despite the numerous technological advances over that past fifteen years, many user problems have not been satisfactorily addressed in regard to SMBG. In particular, many individuals still have difficulty obtaining an adequate blood sample from their finger tip required to effectively measure their blood glucose level. This difficulty can result from fingers being calloused from repeated testing and poor circulation, amongst other factors.

Once a blood sample is obtained, the sample is then transferred to a reagent coated test "strip" that works in combination with the glucose meter. When small blood samples are obtained due to inability to harvest a large enough blood sample, the test strips are frequently wasted and/or the glucose meter will give an inaccurate result. The fingerstick is so problematic in executing effective blood glucose measurement that there are currently over 75 initiatives worldwide being pursued to address or eliminate this problem. Complications in obtaining a blood sample are increased as a normal progressive side effect of the disease and also as the individual naturally ages.

Finally, while numerous prior devices have attempted to address blood collection using traditional large scale tourniquet-type devices, these prior efforts have failed to produce a simple, elegant solution that is low in cost, easy to use with a single hand, and which is especially adapted for use in obtaining blood samples from a smaller extremity such as a fingertip.

SUMMARY OF THE INVENTION

An apparatus used in a method of restricting venous flow in an extremity includes a first flexible, stretchable elongate band and a first flexible, stretchable loop fixed to a first end of the first band. A second loop sized to fit about the extremity is defined by passing a free end of the first band through the first loop. Upon pulling a free end of the first band through the first loop in a direction outward from the extremity, the first band stretches against the first loop, thereby causing the second loop to tighten about the extremity to restrict venous flow therethrough. A combination of frictional engagement and stretching of the first band and of the first loop against each other releasably secures the second loop about the extremity in its tightened position, thereby eliminating the need to hold the apparatus to maintain the tightened position. With venous flow restricted in the extremity, various procedures can be performed such as obtaining a blood sample with a conventional fingerstick puncture of the extremity.

BRIEF DESCRIPTION OF THE DRAWINGS

FIG. 1 is a perspective view of an apparatus of the present invention shown in its pre-use configuration.

FIG. 4 is a plan view of a second embodiment of the apparatus of the present invention.

FIG. 5 is a perspective view of the apparatus of FIG. 4 shown in its pre-use configuration.

DETAILED DESCRIPTION OF THE PREFERRED EMBODIMENTS

Figure 2:
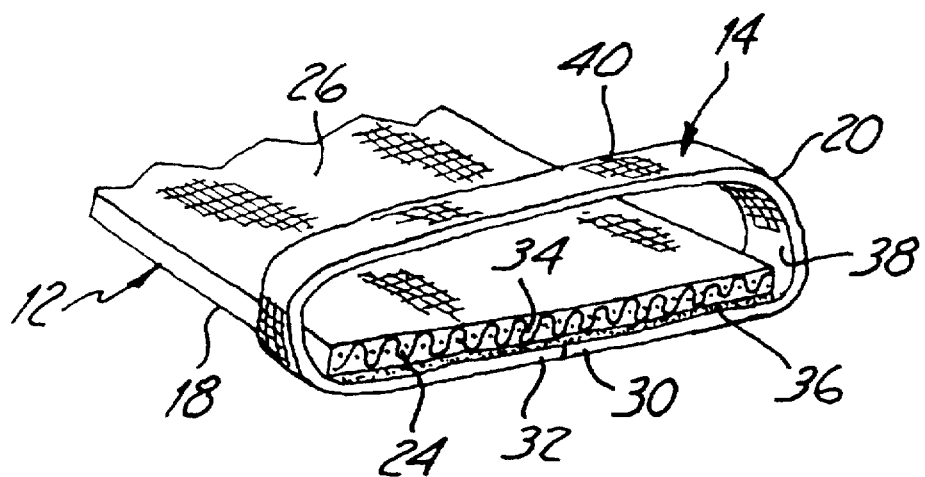
FIG. 2 is a isometric view of an end of the apparatus of FIG. 1 showing its construction.

An apparatus for use in the method of the present invention is illustrated generally in FIG. 1 at 10. Apparatus 10 includes main stretchable band 12 and secondary stretchable band 14. Main band 12 includes free first end 16 and second end 18. Secondary band 14 is fixed to second end 18 of main band 12 to define first loop 20. As shown, main band 12 extends through first loop 20 to define second loop 22. Main band 12 also has first surface 24 and second surface 26.

As shown in FIG. 2, secondary band 14 is attached to main band 12 at second end 18. Secondary band 14 further includes first end 30 and second end 32 while main band 12 further includes edge 34. First end 30 and second end 32 of secondary band 14 are arranged in an end-to-end fashion adjacent main band edge 34 and bonded to first surface 24 of main band 12 with adhesive 36. This arrangement creates first loop 20, which includes inner surface 38 and outer surface 40. Secondary band 14 defining first loop 20 extends in a plane generally transverse to a plane defined by a longitudinal axis of main band 12.

Alternatively, secondary band 14 is attached to end 18 of main band 12 by stitching, interweaving, or fusing, as well as other means of attaching elastic members readily apparent to those skilled in the art.

Secondary band 14 and main band 12 are preferably made of a flexible elastic material and are sized and shaped so that main band 12 is relatively wider and longer than the secondary band 14 to permit second loop 22 to slip over a finger tip or to accommodate the physical dimensions of the body part from which a sample will be extracted. Main band 12 and secondary band 14 also must be sized and shaped in proportion to permit free end 16 of main band 12 to pass freely through first loop 20, as shown in FIG. 1.

Main band 12 preferably has a thickness of about 0.050 inches, a width of about 0.50 inches and a length of about 4 inches. Secondary band 14 preferably has a thickness of about 0.050 inches, a width of about 0.125, and a length of about 1.3 inches. Main band 12 is preferably made of a stretchable elastic band comprised of 49% polyester and 51% rubber while secondary band 14 is preferably made of a stretchable elastic band comprised of 71% polyester and 29% rubber. The material of main band 12 and secondary band 14 is sold under the trademark STRETCHRITE by Rhode Island Textile Company of Pawtucket, R.I. as material number SS64 WHT and SSI 800 WHT, respectively. Adhesive 36 is preferably an adhesive sold under the trademark BEACON SURE BOND by Beacon Chemical Company of Mount Vernon, N.Y. and is of the type well known to those skilled in the art.

In use, apparatus 10 is arranged to form second loop 22 as shown in FIG. 1 by feeding free first end 16 of main band 12 into and through first loop 20 (defined by secondary band 14). The size of secondary loop 22 is adjustable by drawing a selective length of free first end 16 of main band 12 through first loop 20. This adjustability permits use of apparatus 10 on a variety of sizes of body extremities including, but not limited to, fingers, thumbs or toes. It could also be used on the legs or arms of a small child for obtaining a sample of blood or other interstitial fluid. Alternatively, apparatus 10 can be provided in the looped configuration shown in FIG. 1.

Figure 3:
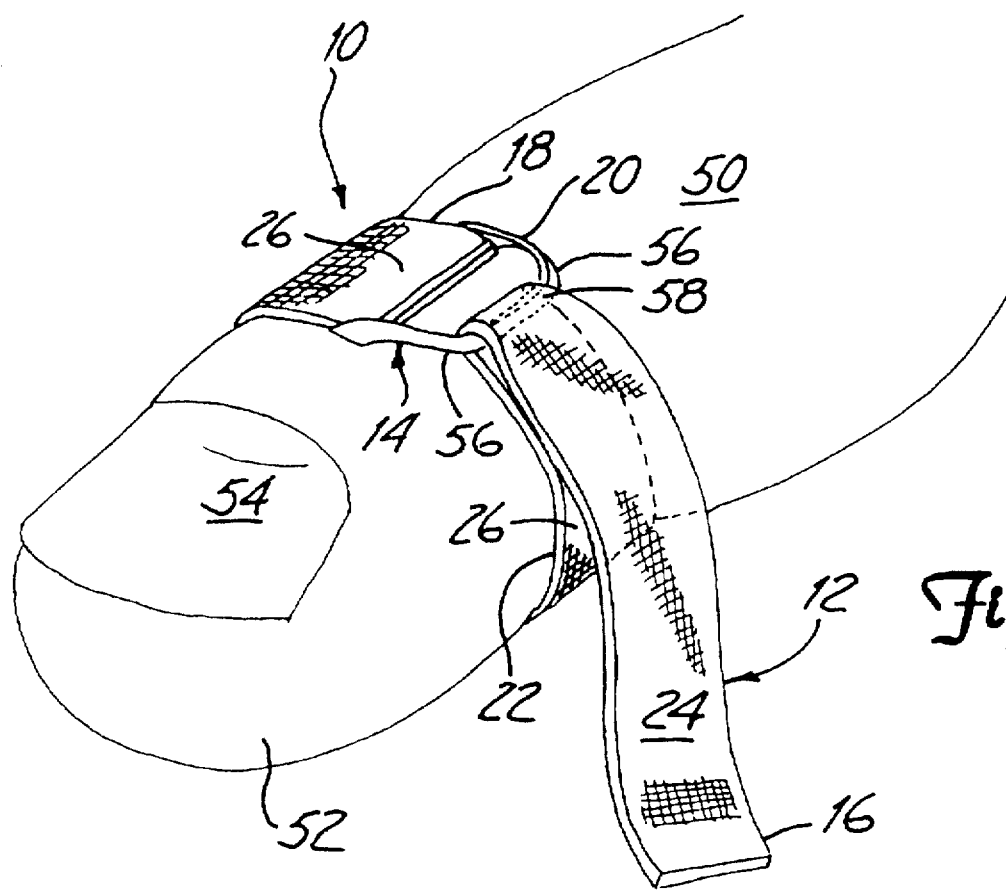
FIG. 3 is a perspective view of the apparatus applied to a finger in a method of the present invention.

Next, second loop 22 is slip fit over and slid along finger 50 to a location along finger 50 proximal to finger tip 52 and finger nail 54, as shown in FIG. 3. With the apparatus 10 in this position, free first end 16 of main band 12 is grasped and pulled back against first loop 20 so that main band 12 extends back over secondary band 14 as shown in FIG. 3 and so that first surface 24 of main band 12 (adjacent free end 16) is exposed. Free end 16 is pulled in this configuration causing main band 12 and secondary band 14 to stretch (i.e. elongate) into the position shown in FIG. 3. In this position, stretched main band 12 becomes releasably fixed relative to stretched first loop 20 (secondary band 14) due to a combination of: (1) the tension between secondary band 14 and main band 12 pulling against each other: and (2) the frictional engagement between outer surface 26 of main band 12 against inner surface of first loop 20, thereby preventing main band 12 from slipping relative to secondary band 14. In addition, the pulling force of main band 12 against secondary band 14 tends to cause a single twist of secondary band 14 in region 56 and causes main band 12 to be pinched at region 58 within stretched first loop 20. This twist of first loop 20, and pinching of main band 12 within stretched first loop 20, further contributes to the temporary locking effect of frictional engagement and tension between stretched secondary band 14 and stretch main band 12. Finally, outer surface 26 of main band and inner surface 38 and outer surface 40 of secondary band 14 preferably have a slightly roughened surface to facilitate their frictional engagment as described above. However, main band 12 and secondary band 14 can be made of a material having a relatively smooth surface (e.g., a rubber elastomer such as a rubber band) that is capable of sufficient frictional engagement between main band 12 and secondary band 14 to cause the releasable locking of main band 12 relative to secondary band 14.

Of course, frictional engagement between the surface of finger 50 and main band 12 further contributes to the ability of main band 12 to become releasably fixed relative to secondary band 14 and to the ability of main band 12 (with secondary band 14) to be releasably fastened about finger 50.

When applied in the manner shown in FIG. 3 and as described above (in which main band 12 becomes releasably locked relative to secondary band 14), both main band 12 and secondary band 14 are stretched with sufficient force to squeeze finger 50 to restrict venous flow in finger tip 52 and to be releasably fastened about finger 50 in this tightened position. This restriction causes blood to be temporarily constrained at finger tip 52 to facilitate obtaining a blood sample at finger tip 52 through a conventional finger stick method (in which finger tip 52 is pricked to produce blood for collection and testing) or other method. The period of time of restriction using apparatus 10 can be anywhere from a few seconds (perhaps 3 seconds) to as long as several minutes (perhaps 5 minutes). In a preferred method, the blood sample obtained at finger tip 52 is used to measure blood glucose or another blood constituent.

Alternatively, free end 16 of main band 12 can be pulled in any direction outward from finger 50 (other than that shown in FIG. 3) that causes both first loop 20 and main band 12 to be stretched with sufficient tension between first loop 20 and main band 12 so that when combined with the frictional engagement between the surfaces of main band 12 and first loop 20 and frictional engagement of main band 12 against finger 50, main band 12 and first loop 20 become releasably locked or fixed relative to each other to maintain second loop 22 in a tightened position about finger 50. For example, free end 16 of main band 12 can be pulled radially outward from finger 50 in a direction generally perpendicular to finger 50 so that the free end 16 of main band 12 would extend upwardly in FIG. 3.

After an appropriate amount of blood is harvested, apparatus 10 is removed from finger 50 by grasping free first end 16 of main band 12 and pulling free end 16 toward a direction opposite that shown in FIG. 3 in order to remove the gripping tension and frictional engagement between main band 12 and secondary band 14. This maneuver releases the pressure applied to finger 50 by apparatus 10 thereby restoring normal venous flow in finger tip 52. Apparatus 10 is then removed from finger 50 by sliding second loop 22 off the finger in the looped configuration ready for its next use.

Although FIG. 3 specifically shows a finger 52, apparatus 10 can be used to restrict venous flow on other smaller extremities (such as thumbs, toes, and/or the limbs of a small child) in which the size of the limb is small enough such that the tension created by the interaction of main band 12 and secondary band 14 is sufficient to restrict venous flow.

The method and apparatus of the present invention has numerous advantages. First, use of the apparatus in the method of the present invention reduces the probability of not getting an adequate blood sample to execute a blood test, thereby reducing the number wasted test strips which in turn reduces the cost ($0.50 to $0.75 per test strip). Reducing the number of repeat fingersticks to get an adequate blood sample would result in less pain for the user through fewer actual fingersticks. In addition, when the glucose test is performed at a doctor's office, hopsital, or other healthcare institution, the reduced number of finger sticks results in direct savings for the institution in terms of fewer wasted test strips. Finally, reducing the number of fingersticks saves time and eliminates time consuming miscellaneous techniques used for accumulating blood in the finger (to obtain a sample) when the conventional fingerstick method is ineffective.

Second, the restriction of venous flow by use of the present invention potentially reduces the depth required to the puncture the finger tip (or other extremity), thereby reducing the probability of the user's tendency to bruise or callous and potentially reduces the pain experienced from the fingerstick puncture. This feature would result in greater comfort for the patient during self-monitoring or during an office visit. Third, the reduction of the necessary puncture depth with the apparatus of the present invention results in greater efficiency in the clinical setting (e.g. per patient processing time for blood testing), which could reduce cost.

Fourth, this restriction in venous flow accomplished by the present invention reduces the difficulty in obtaining a blood sample from the patient's finger, particularly in patient's in which blood sampling is difficult such as when testing someone with compromised circulation (either due to the disease, age or both). Fifth, the apparatus and method of the present invention is superior to other tourniquet-type devices in at least two respects. The apparatus can be deployed and un-deployed using only one hand (either hand) and the elegant simplicity of design makes the apparatus very cost effective to produce in comparison to other tourniquets, which require either relatively complex rigid components or more expensive materials and construction.

This latter advantage of single hand application about the finger tip and single hand tightening and loosening of the device is significant since a large number of people performing a blood glucose test perform these tests at home or their workplace by themselves. Applying a conventional tourniquet or other device that requires knotting or two hands to manipulate the device is clearly inconvenient and not practical for these individuals.

These advantages of the present invention can also be obtained with modifications to the apparatus 10 of the present invention. First, secondary band 12 can be made of a formable or malleable material (for example a thin wire), other than the previously disclosed elastic band. This embodiment of secondary band 14 is not stretchable but which forms into substantially the same shape of secondary band 14 as shown in FIG. 3 when pulling tension of main band 12 is applied against the formable, non-stretchable secondary band 14. In this modified embodiment, the formable, non-stretchable secondary band 14 is attached to end 18 of main band 12 in a manner known to those skilled in the art. The combination of frictional engagement between the formable, non-stretchable secondary band 14 relative to main band 12, and the pulling tension of main band 12 against secondary band 14 causes second loop 22 to remain releasably fastened in a tightened position about finger 50 when free end 16 of main band 12 is released from the user's grasp. The formability of the alternate secondary band 14 facilitates pinching of main band 12 (similar to the pinching of band 12 as shown in FIG. 3) to aid releasable locking of main band 12 relative to secondary band 14.

Another separate modification to apparatus 10 of the present invention also includes replacing the stretchable elastic band defining secondary band 14 with a rigid member having a shape corresponding to the shape of the secondary band shown in FIG. 3 (in which the shaped, rigid secondary band 14 includes a narrow portion for causing pinching of main band 12 as it extends through secondary band 14). A rigid secondary band 14 is made of a suitable rigid material capable of frictional engagement with the surface of main band 14 so that a combination of the frictional engagement between rigid secondary band 14 and main band 12, along with pinching of main band 12 within rigid secondary band 14, and the relative pulling tension between bands 12 and 14, causes second loop 22 to be releasably secured about finger 50 with pressure sufficient to restrict venous flow for obtaining a blood sample.

While not preferred, secondary band 14 can also be replaced by a rigid member having the shape shown in FIG. 2. The material of the rigid member must have a surface facilitating frictional engagement with a surface of main band 12 so that when main band 12 is pulled through the rigid secondary band 14 (having the shape shown in FIG. 2), the frictional engagement of main band 12 against secondary band 14 and the pulling tension of main band 12 against band 14 and against finger 50 causes releaseable fixation of main band 12 relative to secondary band 14 (to thereby releasably secure the second loop 22 about finger 50 with sufficient pressure to restrict venous flow from obtaining a blood sample).

Another alternate embodiment includes an apparatus 70 shown in FIG. 4. As shown in FIG. 4, apparatus 70 includes main flexible elastic band 72 having first end 74 and second end 76. A slit 78 is formed in the main band 72 adjacent second end 76. Slit 78 is oriented generally perpendicular to a longitudinal axis of main band 72. Slit 78 is sized and adapted to permit selective sliding movement of main band 72 through slit 78 and to facilitate selective frictional engagement of main band 72 relative to slit 78. In use, first end 74 of main band 72 is inserted into slit 78 so that main band can be pulled through slit 78 to form loop 80, as shown in FIG. 5. Loop 80 is sized and shaped to fit about a finger 50 (FIG. 3).

In operation, apparatus 70 is used in the manner described in association with FIGS. 1–3 in which the apparatus 70 is placed about finger 50 in its looped configuration (shown in FIG. 5) and first end 74 is grasped and pulled in a direction outward from finger 50 (e.g. radially outward in a direction generally perpendicular to finger 50) until pulling tension of main band 72 and frictional engagement of main band 72 against slit 78 (and against finger 50) releasably secure main band 72 relative to slit 78, thereby releasably securing apparatus 70 in a tightened position about finger 50 with sufficient pressure to restrict venous flow therethrough (for obtaining a blood sample from finger 50).

In the main embodiment, the pulling tension created between main band 12 and secondary band 14 is preferably in a range of 0.15 lbs to 5 lbs. pressure wherein a pressure of 0.75 to 1 lb is the optimal pressure that main band 12 and secondary band 14 place against finger 50 to restrict venous flow through finger 50. This pressure range is sufficient to permit the releasable locking of main band 12 relative to secondary band 14 without causing destruction of apparatus 10.

Although the present invention has been described with reference to preferred embodiments, workers skilled in the art will recognize that changes may be made in form and detail without departing from the spirit and scope of the invention.

We claim:

1. A method of restricting venous flow in a body extremity comprising:

providing an adjustably sized main loop adapted to fit about a tip of an extremity and defined by a main flexible stretchable band having a first end extending through a secondary loop defined at a second end of the main band the main loop and the second loop having surfaces adapted for frictional engagement with each other;

sliding the main loop over about a tip of the extremity;

pulling the first end of the main band further through the secondary loop and in a direction outward from the extremity so that the main band stretches and causes stretching of the secondary loop, thereby causing the main loop to tighten about the extremity with sufficient pressure to restrict venous flow of blood through the tip of the extremity, wherein a combination of stretching of the main loop and of the secondary loop against each other in tension, and of frictional engagement of the main loop against the secondary loop releasably secures the main loop relative to the secondary loop to releasably secure the main loop about the extremity in the tightened position to restrict venous flow, whereupon the tightened position is maintained upon release of the free first end of the main band.

2. The method of claim 1 wherein the secondary loop is comprised of a flexible stretchable material.

3. The method of claim 1 wherein the secondary loop is comprised of a non-stretchable, formable material.

4. The method of claim 1 wherein the secondary loop is comprised of a rigid material and has a shape configured and arranged to facilitate releasably securable engagement with the main band.

5. The method of claim 1 wherein the secondary loop is defined by a plane that is generally transverse relative to a plane defined by a longitudinal axis of the main band.

6. A method of obtaining a blood sample from a body extremity comprising:

inserting a first end of a main band into and through a first loop, defined at a second end of the main band by a second band, to define a second loop sized to fit about a tip of the body extremity;

positioning the second loop over a tip of the extremity and sliding the second loop over the extremity tip;

pulling the first end of the main band further through the first loop with a single hand so that the main band stretches and causes stretching of the first loop, thereby causing the second loop to tighten about the extremity with sufficient pressure against the extremity to restrict venous flow of blood through the tip of the extremity, wherein a combination of the stretching of main band and first loop and of frictional engagement of the main band against the first loop releasably secures the main band relative to the first loop to releasably secure the second loop about the extremity in the tightened position;

pricking the tip of the extremity tip on a side of the second loop distal to the tightened second loop to draw a blood sample from the extremity tip;

releasing the second loop of the apparatus about the extremity by pulling the first end of the main band in a manner to release frictional engagement and tension between the main band and the first loop.

7. The method of claim 6 wherein the tension of the main band and the tension of the first loop pulling against each other causes a portion of the main band to become pinched within the first loop and causes a portion of the first loop to twist, wherein both the pinching of the main band and the tensioning of the first loop further releasably secure the main band relative to the first loop.

8. A method of obtaining a blood sample from a finger comprising:

inserting a first end of a main stretchable band into and through a first loop at a second end of the main band to thereby define a second loop sized to fit about a finger tip, the first loop being defined by a secondary stretchable band fixed to the second end of the main band;

positioning the second loop about a finger adjacent a finger tip;

pulling the first end of the main band through the first loop with a single hand in a direction so that the main band extends back over the first loop to cause a portion of the main band to frictionally engage and to stretch the first loop and to cause the main band to stretch, thereby tightening the second loop about the finger, wherein the frictional engagement of the first loop against the main band and the tension of the first loop pulling stretched main band against the surface of the finger securely and releasably fastens the second loop about the finger with sufficient pressure applied against the finger to restrict venous flow blood through the finger tip;

releasing the first end of the main band whereupon the second loop remains releasably fastened about the finger;

pricking the finger tip on a side of the finger distal to the tightened second loop about the finger to draw a blood sample from the finger tip;

releasing the second loop about the finger by pulling the first end of the main band in a direction to release the frictional engagement and stretching tension of the main band against the first loop to cause the main band to slip relative to the first loop.

* * * * *